United States Patent [19]
Ham et al.

[11] 3,933,026
[45] Jan. 20, 1976

[54] ULTRASONIC CALIBRATION STANDARD

[76] Inventors: William C. Ham, 360 Panoramic Way, Apt. F; Francis J. Dodd, 2228 Dwight Way, No. 4, both of Berkeley, Calif. 94704; Spencer J. Friedrick, 1349 Rose St., Apt. C, Berkeley, Calif. 94702

[22] Filed: July 31, 1974

[21] Appl. No.: 493,446

[52] U.S. Cl. .................................. 73/1 R; 73/67.8 S
[51] Int. Cl.² .......................................... G01N 29/04
[58] Field of Search .. 73/1 DV, 1 R, 67.8 S, 67.8 R; 219/69 R, 69 M; 138/111; 60/39.66, 267

[56] References Cited
UNITED STATES PATENTS

| | | | |
|---|---|---|---|
| 1,405,482 | 2/1922 | Bostedo | 60/267 X |
| 3,276,205 | 10/1966 | Reisman et al. | 60/39.66 X |

FOREIGN PATENTS OR APPLICATIONS

| | | | |
|---|---|---|---|
| 684,276 | 4/1964 | Canada | 138/111 |
| 18,690 | 8/1894 | United Kingdom | 138/111 |

OTHER PUBLICATIONS
"A Proposed Resolution Test For Ultrasonic Angle Beam Probes" by Chapman, from Materials Evaluation 1–71.

*Primary Examiner*—James J. Gill
*Attorney, Agent, or Firm*—Townsend and Townsend

[57] ABSTRACT

A calibration standard for an ultrasonic inspection system used to test components having curved surfaces. Several embodiments are disclosed, all having at least one curved surface and a calibration hole providing an internal controlled geometry reflector surface having a body axis which conforms to the curvature of the surface. The several embodiments can be manufactured by several methods, one of which comprises securing a block of electrically conductive material having the desired curved surface in a fixture, placing a moveable electrically conductive electrode adjacent the block to form a gap therebetween, applying a high voltage to the block and the electrode to cause an electrical discharge across the gap while bathing the gap in a dielectric fluid, and advancing the electrode into the interior of the block along a curved path having a center of curvature common to the center of curvature of the curved surface to form an internal bore therein.

11 Claims, 12 Drawing Figures

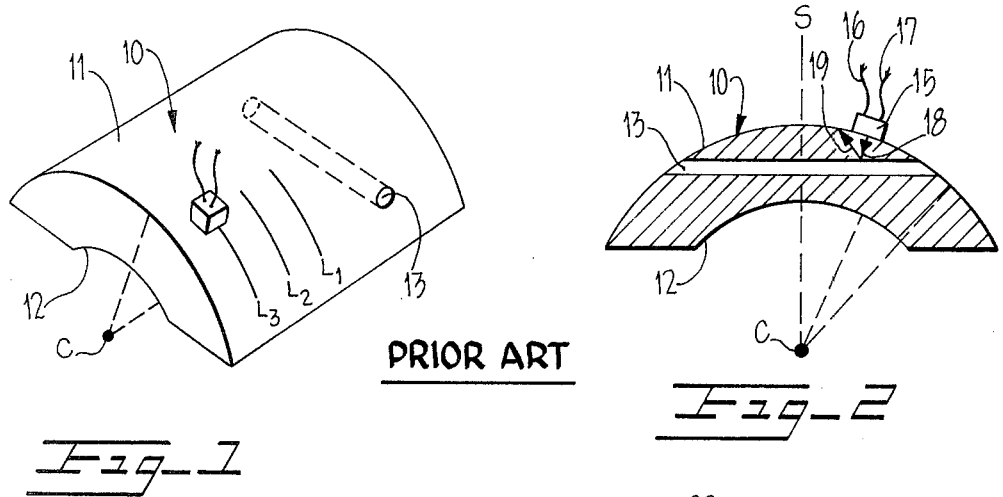
PRIOR ART
Fig-1
Fig-2
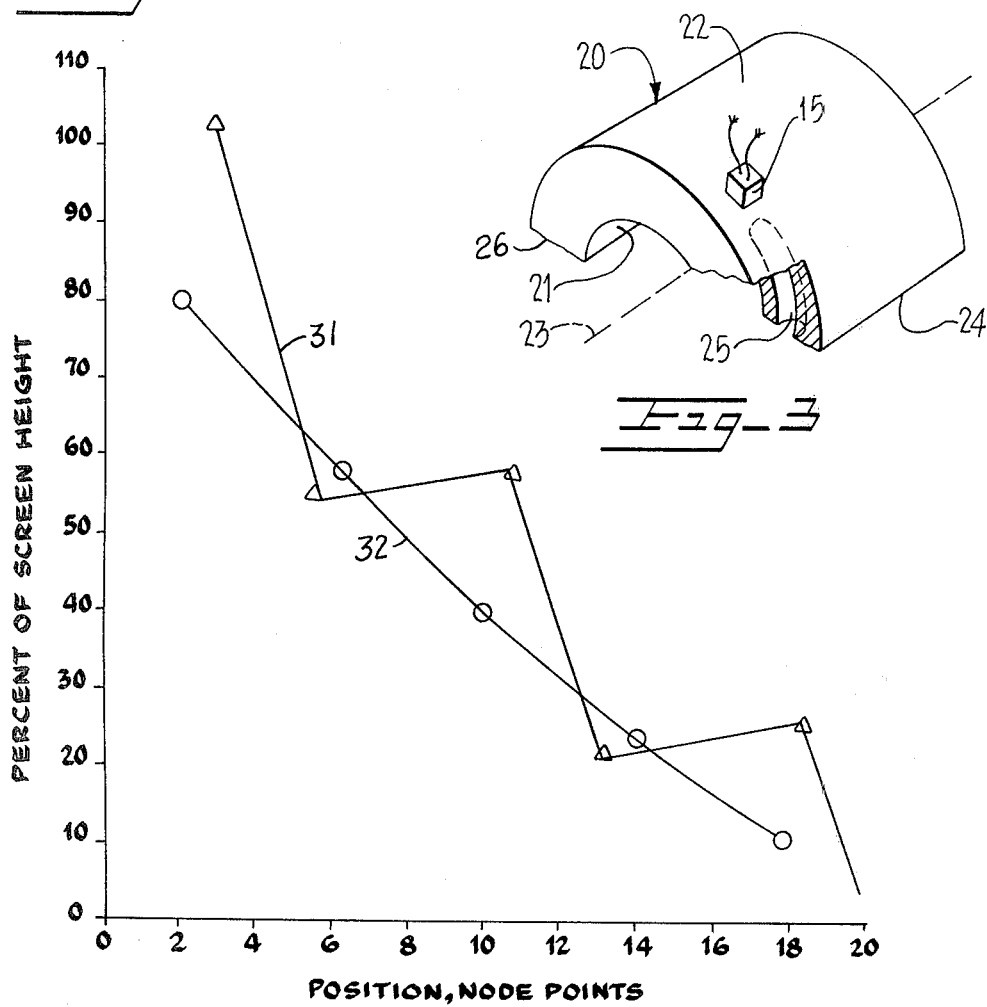
Fig-3
O = PIPE SECTION, CURVED HOLE (CALIBRATION).
△ = PIPE SECTION, STRAIGHT HOLE, TRANSDUCER STRAIGHT.
Fig-4

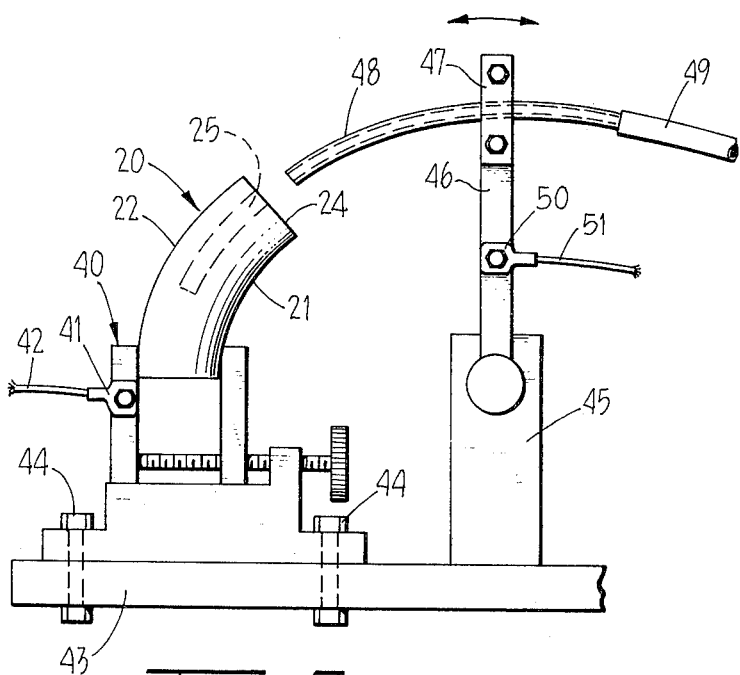
Fig_5
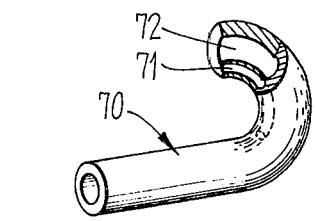
Fig_7
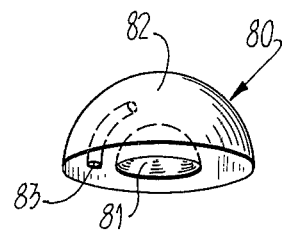
Fig_8
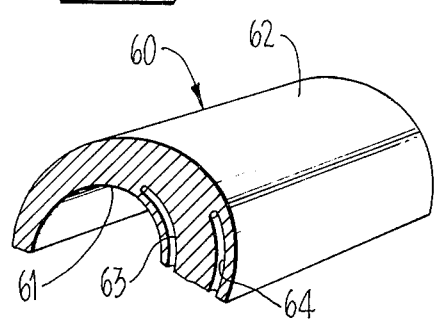
Fig_6
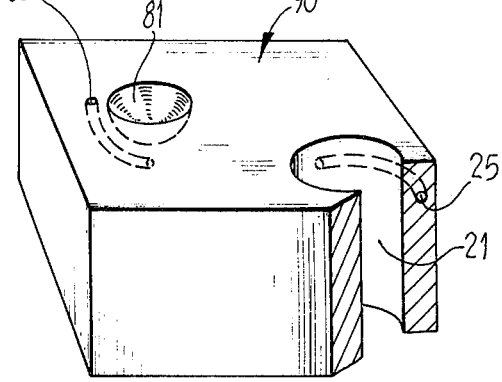
Fig_9
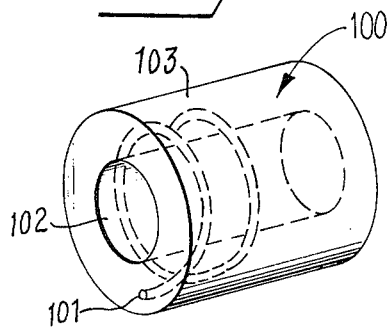
Fig_10
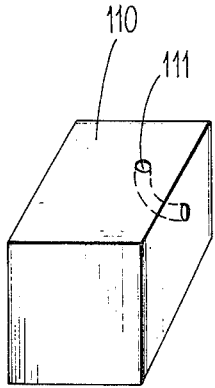
Fig_11
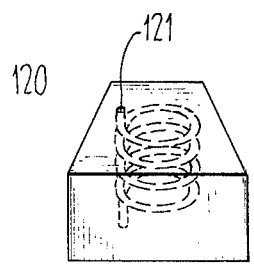
Fig_12

3,933,026

ULTRASONIC CALIBRATION STANDARD

BACKGROUND OF THE INVENTION

This invention relates to ultrasonic inspection of materials. More particularly, this invention relates to calibration standards employed with ultrasonic testing systems.

Ultrasonic inspection is widely used for the nondestructive testing of many types of materials, such as pipes, pressure vessels, welds, conduits and the like. In a typical ultrasonic testing procedure, a transducer operable in the ultrasonic range is placed on a surface of the component being tested and repeatedly energized to create pulsed ultrasonic waves which are coupled to the interior of the component. The waves travel through the interior of the component, and are reflected at surfaces or interior discontinuities and subsequently detected by either the same transducer operated in a receiving mode or a second transducer at the same location as the generating transducer or a different location spaced therefrom. By noting the arrival time and intensity of the received sound waves, cracks, fissures, or other inhomogenieties in the interior of the component can be detected.

In order to correctly interpret the received waves, the inspection apparatus must be calibrated by means of a calibration standard. A typical calibration standard is constructed from the same or a similar material to that from which the components to be tested are fabricated, and is provided with a controlled geometry reflector, such as a cylindrical hole of precise dimensions. In use, the transducer of the inspection system to be calibrated is placed on a surface of the calibration standard at a known distance from the calibration reflector and energized to generate pulsed ultrasonic waves in the interior of the calibration standard. By measuring the time interval between pulse generation and reception of the reflected wave, the speed of the waves in the particular material can be determined. This information enables the distance between the transducer and a reflector surface in a component under inspection to be determined from the time interval between pulse generation and reception. In addition, by measuring the attenuation of the wave in traveling through the calibration standard from the sending transducer to the reflector and to the receiving transducer, a calibration scale showing the attenuation of the ultrasonic waves with distance in the material, commonly termed "a distance amplitude correction scale" or DAC, can be plotted.

While existing calibration standards of the above type have been found to be adequate for components having planar surfaces, in applications requiring the ultrasonic inspection of components having curved surfaces such standards have been found to lead to inaccurate results. In known calibration standards used with curved surfaces, the calibration hole containing the controlled geometry reflector surfaces is a cylindrical bore passing through the body of the calibration standard. Due to the internal geometries of the curved calibration standard reflecting surfaces, the resulting DAC plot obtained is much less accurate than that obtained when planar surfaces are involved.

The present day practice of using a straight calibration hole in a curved calibration standard thus exhibits three serious disadvantages. Firstly, the amplitude of ultrasonic waves reflected from the controlled geometry reflector surface is a function of transducer position with respect to the line of symmetry perpendicular to the calibration hole. Secondly, a continuous DAC plot cannot be obtained due to unavoidable focusing and defocusing of the beam caused by the curved calibration standard surfaces. Lastly, the location of the reflector surface within the calibration standard material cannot be accurately determined since the transducer to reflector distance varies across the width of the ultrasonic beam. Efforts to overcome these disadvantages in the past have not met with wide success.

SUMMARY OF THE INVENTION

The invention comprises an ultrasonic calibration standard having at least one curved surface and a calibration hole having a body axis which conforms to the curvature of the surface. In a first embodiment of the invention, the calibration standard comprises an arcuate segment of cylindrical pipe with a calibration hole having an axis lying on a circular path whose center of curvature is substantially equal to the center of curvature of the inner and outer cylindrical pipe surfaces. In a second embodiment, the calibration standard comprises a pipe section having a U-bend with a calibration hole which follows the curvature of the inside radius wall of the U-bend. In still another embodiment, the calibration standard comprises a block of material having inner and outer curved surfaces of different contours and a pair of calibration holes each following the curvature of a different one of the inner and outer surfaces. In still another embodiment, the calibration standard comprises a generally spherical cap with a calibration hole having a curvature substantially equal to the curvature of the sphere. In still another embodiment, the calibration standard comprises a block of material having a cylindrical hole with a calibration hole which follows the contour of the hole wall surface. In still another embodiment, the calibration standard comprises a block of material having a spherical depression with a calibration hole in the material which follows the contour of the sphere. In still another embodiment, the calibration standard comprises a cylindrical pipe section with a spiral calibration hole in the annular regions thereof, the calibration hole curvature following the curvature of the pipe walls.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a perspective view illustrating a known curved calibration standard having a straight hole;

FIG. 2 is a sectional view taken along lines 22 of FIG. 1;

FIG. 3 is a perspective view partially in section showing a first embodiment of the invention;

FIG. 4 is a DAC plot comparing the prior art with the instant invention;

FIG. 5 is a schematic view of an apparatus for fabricating the FIG. 2 embodiment; and FIGS. 6–12 illustrate alternate embodiments of the invention.

DESCRIPTION OF THE PREFERRED EMBODIMENT

Turning now to the drawings, FIGS. 1 and 2 illustrate a typical calibration standard of the type currently employed to calibrate an ultrasonic inspection apparatus prior to the testing of pipe sections or similar cylindrical objects. The standard comprises an arcuate section 10 having outer and inner wall surfaces 11, 12, respectively, with substantially the same center of curvature C. The calibration hole 13 is a straight substantially cylindrical hole formed in material 10 at substantially right angles to the body axis of the material.

In use, a conventional ultrasonic transducer 15 having a pair of leads 16, 17 coupled to a conventional ultrasonic inspection apparatus is placed on outer surface 11 and the apparatus is calibrated by pulsing transducer 15, sensing the reflected waves from the reflector surface of calibration hole 13, and measuring the travel time and amplitude of the ultrasonic waves at spaced locations $L_1$, $L_2$, and $L_3$ along surface 11 in a conventional manner. As suggested by arrows 18, 19, depending on the location of transducer 15 relative to the axis of symmetry S of the calibration standard, a major portion of the ultrasonic waves reflected from the surface of calibration hole 13 are reflected at such a large angle that the returning waves corresponding thereto do not strike the sensing face of transducer 15. As a result, the amplitude of reflected waves which are received by transducer 15 varies with position L and the angle subtended by axis S and transducer 15, which renders the resulting DAC plot inaccurate.

FIG. 3 shows a first embodiment of the invention suitable for use in calibrating an ultrasonic inspection apparatus prior to the testing of circular pipe or similar cylindrical objects. An arcuate section of material 20 has inner and outer walls 21, 22, respectively, with the center of curvature of both wall surfaces 21, 22, coincident with the body axis 23. Unlike the prior art standard, calibration standard 20 is provided with a calibration hole 25 which is preferably substantially cylindrical in cross section and which has a contour which follows the contour of wall surfaces 21, 22. Calibration hole 25 may terminate internally of material 20 as depicted, or may extend entirely from edge 24 to edge 26.

FIG. 4 shows a pair of DAC plots obtained with the prior art calibration standard shown in FIGS. 1 and 2 and the first embodiment of the invention shown in FIG. 3. In FIG. 3, the ordinate represents the amplitude of reflected pulses received by transducer 15 while the abscissa represents the distance of transducer 15 from the calibration hole along the body axis of the calibration standard measured in node points. Curve 31 is a DAC plot obtained with the straight hole calibration standard shown in FIGS. 1 and 2, while curve 32 illustrates the DAC plot obtained with the calibration standard shown in FIG. 3. A comparison of these two curves shows that not only signal strength but also the apparent position of the calibration hole are inaccurately registered with the prior art standard. The DAC plot obtained with the FIG. 3 embodiment, on the other hand, accurately depicts both transducer position and signal attenuation in traveling through the material 20.

FIG. 5 is a schematic elevational view illustrating a fixture for fabricating a calibration standard of the type shown in FIG. 3. A curved solid block of material 20 preformed with inner and outer walls 21, 22 is secured in a suitable clamp 40 constructed from an electrically conductive material. Clamp 40 is provided with a conductive electrode 41 coupled via a conductor 42 to ground potential of an associated high voltage power supply (not illustrated). Clamp 40 is mounted on a rigid base member 43 by means of a pair of bolts 44.

Secured to an insulated mounting post 45 supported by base member 43 is a pivotable electrode arm 46 having a suitably configured clamp 47 at the free end thereof for supporting an active electrode 48. Electrode 48 is a hollow conductive member preformed to the desired arcuate shape (e. g. circular arcuate) and is coupled to a conventional source of dielectric fluid by means of hollow tubing 49. Electrode arm 46 is provided with a high voltage connector 50 which is coupled via a conductive lead 51 to the high voltage output terminal of the high voltage source.

In operation, material 20 is placed in clamp 40 and secured thereto. Electrode 48 is then positioned in clamp 47 at a radial position along arm 46 corresponding to the desired position of the calibration hole 25 to be formed in material 20. The associated dielectric fluid supply is then actuated to supply a flow of dielectric fluid through electrode 48 to the tip thereof, after which high voltage is applied via elements, 51, 50, 46, 47 and 48 to the tip of electrode 48. Arm 46 is then maneuvered in the counterclockwise direction at a controlled rate to position the tip of electrode 48 closely adjacent the end surface 24 of material 20 to establish a small discharge gap thereacross. The resulting spark discharge melts a portion of the material 20 which is flushed away by the dielectric fluid flowing in electrode 48. Thereafter, electrode 48 is advanced at a predetermined rate to form calibration hole 25. This process continues until calibration hole 25 has achieved the desired length, after which the high voltage is removed from electrode 48, and electrode 48 is withdrawn from the now formed hole.

If desired, the FIG. 5 apparatus may be modified so that electrode 48 is stationary and material block 20 is movable with equally beneficial results.

The calibration standard may also be manufactured by other known methods. For example, a rectangular block of material of the desired thickness may first be provided with a bore by drilling. Thereafter, the material is heated to a temperature at which the material will readily creep, usually a temperature in the neighborhood of 0.5 $T_m$, where $T_m$ is the melting temperature of the material, after which the rectangular block may be formed to the desired curved shape. In another method of fabricating the calibration standard, a block of material having the desired curved shape is electrochemically machined to form the calibration bore.

FIGS. 6–12 illustrate alternate embodiments of the invention suitable for use as calibration standards for components of various curved shapes. FIG. 6 illustrates a calibration standard 60 for cylindrical materials in which the axis of the inner cylindrical wall surface 61 is offset from the axis of the outer cylindrical wall surface 62. In this embodiment, a pair of calibration holes are provided: a first hole 63 having a curvature which follows the curvature of the inner wall surface, and a second hole 64 having a curvature following the curvature of the outer wall surface.

FIG. 7 illustrates a calibration standard 70 suitable for use with pipes having a U-bend. In this embodiment, the calibration hole 71 follows the curvature of the inside radius wall 72 of the U-bend.

FIG. 8 illustrates a calibration standard 80 suitable for use with spherical cap materials having concentric inner and outer wall surfaces 81, 82. In this embodiment, the calibration hole 83 follows the curvature of the concentric spherical wall surfaces.

FIG. 9 illustrates a calibration standard 90 for use with both cylindrical wall surfaces and spherical depressions.

As will be apparent to those skilled in the art, the calibration holes provided in the FIG. 6–9 embodiments can all be formed with the apparatus shown in FIG. 5.

FIG. 10 illustrates still another embodiment of the calibration standard 100 in which the calibration hole 101 is in the shape of a helix symmetrically formed with respect to the center of curvature of the inner and outer cylindrical wall surfaces 102, 103. This type of calibration hole may be formed with a modified version of the apparatus formed in FIG. 5 supplemented with an axial feed device for feeding arm 46 into the plane of the Fig. at a predetermined rate.

FIG. 11 illustrates a calibration standard 110 in which the calibration hole 111 is formed in a rectangular block of material to the desired curved shape, the hole extending from the top surface of the block, interiorly thereof, and terminating in a side wall.

FIG. 12 shows a calibration standard having a helical bore 121 extending from the top surface, internally of the block of material and terminating in the bottom surface.

As will now be apparent, calibration standards constructed in accordance with the teachings of the invention provide an accurate means for calibrating an ultrasonic inspection system prior to testing components having curved surfaces. As will be apparent to those skilled in the art, the invention may be employed with other curved surfaces than cylindrical or spherical surfaces. For example, if desired, calibration holes having parabolic, hyperbolic or other curved shapes may be provided to meet the requirements of particular applications. Calibration holes of this type may be most readily fabricated by the creep forming process noted supra.

While the above provides a complete disclosure of the preferred embodiments of the invention, various modifications, alternate constructions and equivalents may be employed without departing from the true spirit and scope of the invention. For example, the fixture shown in FIG. 5 may be provided with an automatic feed mechanism, if desired, to control the movement of arm 46 and active electrode 48. In addition, holes having other cross-sectional shapes than circular, e.g. square, rectangular, star-shaped and the like, may be provided if desired to meet the requirements of a particular application. Accordingly, the above description and illustrations should not be construed as limiting the scope of the invention which is defined by the appended claims.

What is claimed is:

1. An improved ultrasonic calibration standard for use in calibrating an ultrasonic inspection system for testing components fabricated from a component material having known ultrasonic wave propagating properties, said standard comprising a solid monolithic block fabricated from a material having ultrasonic wave propagating properties substantially similar to said component material, said block having at least one curved surface of predetermined curvature and means for providing an internal controlled geometry ultrasonic wave reflector surface, said means including a bore formed internally of said block and having a curved longitudinal axis, the curvature of said longitudinal axis following the curvature of said curved surface so that the perpendicular distance between said curved surface of said block and all points lying on a line on the surface of said bore drawn parallel to said longitudinal axis is substantially constant.

2. The device of claim 1 wherein the curvature of said curved surface and the curvature of said longitudinal axis of said bore are substantially right circular cylindrical with a common center of curvature.

3. The device of claim 1 wherein said curved surface is substantially partially spherical and the curvature of the longitudinal axis of said bore is circular arcuate, said curved surface and said axis curvature having a common center of curvature.

4. The device of claim 1 further including a second curved surface and a second internally formed bore, the curvature of the longitudinal axis of said second bore following the ccurvature of said second curved surface.

5. The device of claim 4 wherein said first curved surface and the curvature of said longitudinal axis of said first bore are substantially right circular cylindrical with a common center of curvature, and wherein said second curved surface is substantially partially spherical and the curvature of said longitudinal axis of said second bore is circular arcuate, said second curved surface and the axis of said second bore having a common center of curvature.

6. The device of claim 4 wherein said first curved surface and the curvature of said longitudinal axis of said first bore are substantially right circular cylindrical with a common center of curvature, and wherein said second curved surface and the curvature of the longitudinal axis of said second bore are substantially right circular cylindrical with a common center of curvature, the center of curvature of said first curved surface and the axis of said first bore being different from said center of curvature of said second curved surface and the axis of said second bore.

7. The device of claim 1 wherein said calibration standard comprises a substantially cylindrical annular member having a U-bend along a portion thereof, said first curved surface comprising the inner wall of said annular member along said U-bend portion and the axis of said first internally formed bore following the curvature of said inner wall.

8. The device of claim 1 wherein said calibration standard comprises a cylindrical annular member, said first curved surface comprises the inner wall surface of said annular member, and said internally formed bore forms a helix whose center of curvature is common to the center of curvature of said inner wall surface.

9. A method of fabricating a calibration standard for use in calibrating an ultrasonic inspection system, said calibration standard having at least one curved surface conforming to a curved surface of components to be inspected by said system, said method comprising the steps of:
 a. securing a block of electrically conductive material having said curved surface in a fixture;
 b. placing a moveable electrically conductive electrode adjacent said block to form a gap therebetween;
 c. applying a high voltage to said block and said electrode to cause an electrical discharge across said gap while bathing said gap in a dielectric fluid; and
 d. repeating said step (c) while advancing said electrode into the interior of said block along a curved path having a center of curvature common to the center of curvature of said curved surface to form a bore within said block providing a controlled geometry reflector surface.

10. The method of claim 3 wherein said curved surface is substantially right circular cylindrical and said step (d) includes the step of advancing said electrode along a substantially right circular cylindrical path.

11. The method of claim 10 wherein said step (d) further includes the step of translating said electrode along the axis of said cylindrical surface to form a helical bore in said block.

\* \* \* \* \*